(12) United States Patent
Han

(10) Patent No.: US 8,809,034 B2
(45) Date of Patent: Aug. 19, 2014

(54) **METHOD FOR CULTURING *MYCOPLASMA* CONTAMINATION-FREE CELLS AND METHOD FOR REMOVING *MYCOPLASMA* CONTAMINATION OF CELLS**

(71) Applicant: Jae-Jin Han, Gyeonggi-do (KR)

(72) Inventor: Jae-Jin Han, Gyeonggi-do (KR)

(73) Assignee: Cellsafe Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/090,768

(22) Filed: Nov. 26, 2013

(65) Prior Publication Data

US 2014/0093955 A1    Apr. 3, 2014

Related U.S. Application Data

(62) Division of application No. 13/513,743, filed as application No. PCT/KR2010/008342 on Nov. 24, 2010.

(30) Foreign Application Priority Data

Dec. 8, 2009  (KR) ........................ 10-2009-0121103

(51) Int. Cl.
*C12N 1/00*    (2006.01)

(52) U.S. Cl.
USPC .............................. 435/243; 435/41; 435/244

(58) Field of Classification Search
CPC ....... C12N 1/14; C12N 5/0018; C12Q 5/0018
USPC .......................................... 435/41, 243, 244
See application file for complete search history.

(56) References Cited

PUBLICATIONS

Houdai, T. et al. "Hairpin conformation of amphidinols possibly accounting for potent membrane permeabilizing activities", Tetrahedron. vol. 61 (11), pp. 2795-2802 (Mar. 14, 2005).
Goldstein, N. I. et al. "In Vitro Anti-Mycoplasmal Activity of Amphotericin B Methyl Ester", Journal of Antibiotics (Tokyo). vol. 29 (6), pp. 656-661 (Jun. 1976).
Uphoff, C. and Drexler, H. "Elimination of mycoplasma from infected cell lines using antibiotics", Cancer Cell Culture: Methods in Molecular Medicine, 2004, vol. 88, VII, p. 329.
Lampen, J. O. et al. "Inhibition of the Pleuropneumonia-Like Organism Mycoplasma Gallisepticum by Certain Polyene Antifungal Antibiotics", Journal of Bacteriology. vol. 86, pp. 945-949 (Nov. 1963).
Béven, L. et al. "Membrane Permeabilisation and Antimycoplasmic Activity of the 18-residue Peptaibols, Trichorzins PA", Biochimica et Biophysica Acta. vol. 1372(1), pp. 78-90 (Jun. 24, 1998).
Paul, G. K. et al., "Chemical Structures of Amphidinols 5 and 6 Isolated from Marine Dinoflagellate *Amphidinium klebsii* and Their Cholesterol-Dependent Membrane Disruption", J. Mar. Biotechnology (1997) 5: 124-128.
Houdai, T. et al., "Acetate Labeling Patterns of Dinoflagellate Polyketides, Amphidinols 2, 3 and 4", Tetrahedron 57 (2001) 5551-5555.
Echigoya, R. et al., "The Structures of Five New Antifungal and Hemolytic Amphidinol Analogs from *Amphidinium carterae* Collected in New Zealand", Harmful Algae 4 (2005) 383-389.

*Primary Examiner* — Susan Hanley
*Assistant Examiner* — Nghi Nguyen
(74) *Attorney, Agent, or Firm* — Vorys, Sater, Seymour and Pease LLP; Mihsun Koh

(57) ABSTRACT

Provided is a method for culturing cells, which prevents the possibility of *mycoplasma* contamination by culturing the cells using biomass extract obtained by culturing a strain with amphidinol productivity, preferably a strain such as *Amphidinium klebsii, Amphididinium carterae*, and the like belonging to Dinoflagellates, or using a fraction obtained from the extract; and a method for removing *mycoplasma* contamination of the cells by culturing the cells contaminated by *mycoplasma* using the amphidinol derivatives. In addition, provided is a method for removing *mycoplasma* contamination of the cells, including a combination of single cell-isolating enzyme solution treatment and cell aggregate removal.

6 Claims, 2 Drawing Sheets

METHOD FOR CULTURING *MYCOPLASMA* CONTAMINATION-FREE CELLS AND METHOD FOR REMOVING *MYCOPLASMA* CONTAMINATION OF CELLS

This is a Divisional Application filed under 35 U.S.C. §120 as a divisional of U.S. patent application Ser. No. 13/513,743, filed on Jun. 4, 2012, which was a National Phase Application filed under 35 U.S.C. §371 of PCT/KR2010/008342, filed on Nov. 24, 2010, an application claiming the benefit under 35 U.S.C. §119 of Korean Application No. 10-2009-0121103, filed on Dec. 8, 2009, the content of each of which is hereby incorporated by reference in their entirety.

TECHNICAL FIELD

The present invention relates to a cell culturing method for preventing *mycoplasma* contamination possibility by culturing cells using an extract of a biomass obtained by culturing an amphidinol-producing strain or a fraction obtained from the extract; and to a method for removing *mycoplasma* contamination from cells contaminated with *mycoplasma* by culturing the cells using the extract or fraction. And also, the present invention relates to a method for removing *mycoplasma* contamination from cells contaminated with *mycoplasma*, the method comprising treating with an enzyme solution for single cell-isolation and removing cell clumps.

BACKGROUND ART

*Mycoplasma*, belonging to the class Mollicutes, is a bacterium that does not have cell wall. *Mycoplasma* has a size of about 0.2 to 0.8 μm and can pass through a 0.2 μm filter. Typically, *mycoplasma* contaminates cells during cell culturing, and in particular, *mycoplasma*, such as *Mycoplasma hyorhinis, Mycoplasma fermentans, Mycoplasma orale, Mycoplasma argininii, Mycoplasma hominis,* or *Acholeplasma laidlawi*, contaminates cells during cell culturing in pharmaceutical companies, hospitals, and college laboratories where cell culturing is frequently conducted. In general, *mycoplasma* contaminations occur during cell line construction from a living organism infected with *mycoplasma*, and furthermore, serum and carelessness in laboratories bring about contaminations between cell lines, thereby resulting in *mycoplasma* contamination all over the laboratories.

Reportedly, in the USA, about 15% of cell lines are contaminated with one or more species of *mycoplasma*. Such a large proportion may be due to the fact that *mycoplasma* is not accompanied with visible changes, such as an increase in a turbidity of a medium as in the case of other infection sources (i.e., bacteria having cell wall or fungi), or cell death as in the case of virus. Thus, experimenters fail to recognize the contamination and spread the contamination. Also, due to the absence of cell wall, *mycoplasma* is not affected by penicillin and other beta lactam antibiotics which are typically used in culturing cells.

Although *mycoplasma* contamination is not accompanied with visible changes in culturing cells, it causes various unpredictable outcomes. One of the most representative unpredictable outcomes is induction of abnormal cytokine expression in cell lines by changing the metabolism of infected cell line. Therefore, many experiments and studies produce abnormal results stemming from the *mycoplasma* contamination. Also, *mycoplasma* may change the shape of cells, and may consume a metabolite required to synthesize DNA or RNA, thereby affecting a metabolism of nucleic acids. Therefore, conformation of receptors or membrane proteins on cell membrane are changed, and thus, cellular immunity or a signal transmission system are disturbed and cell growing rates are changed, thereby causing unpredictable results for example in cell-growth studies or cytotoxicity studies. Also, *mycoplasma* contamination changes nucleic acid metabolism and/or metabolism of infected cell line, and thus, virus production using the infected cell line is also reduced. In particular, when a monoclonal antibody is produced, the fusion rate of hybridoma cells may be decreased, and also, antibody production is substantially decreased, leading to failures of experiments. Such phenomena may negatively affect production of biological preparations, for example, a vaccine. This shows that *mycoplasma* contamination causes serious problems even in respect to economy.

Despite such problems stemming from serious *mycoplasma* contamination accompanied with cell culturing, a method for removing the *mycoplasma* contamination to a satisfactory level has not been developed. Typically, the *mycoplasma* contamination is removed by using tetracycline or quinolone antibiotics, or by using non-antibiotics such as peptide and lipopeptide. In these cases, however, the *mycoplasma* contamination is not completely removed, and also, when these materials are used at a high concentration for complete removal, cytotoxicity or antibiotic resistance may occur.

DISCLOSURE

Technical Problem

The present invention provides a cell culturing method for preventing *mycoplasma* contamination possibility by culturing cells using an extract of a biomass obtained by culturing an amphidinol-producing strain or a fraction obtained from the extract The present invention also provides a method for removing *mycoplasma* contamination from cells contaminated with *mycoplasma* by culturing the cells using the extract or fraction.

The present invention also provides a method for removing *mycoplasma* contamination from cells contaminated with *mycoplasma*, the method comprising treating with an enzyme solution for single cell-isolation and removing cell clumps.

Technical Solution

In accordance with an aspect of the present invention, there is provided a cell culturing method for preventing *mycoplasma* contamination, the cell culturing method comprising culturing cells in a medium that comprises an extract of biomass obtained by culturing an amphidinol-producing strain, preferably *Amphidinium klebsii* or *Amphidinium carterae*; or a fraction obtained from the extract.

In accordance with another aspect of the present invention, there is provided a method for removing *mycoplasma* contamination from cells contaminated with *mycoplasma*, the method comprising culturing cells contaminated with *mycoplasma* in a medium that comprises an extract of biomass obtained by culturing an amphidinol-producing strain, preferably *Amphidinium klebsii* or *Amphidinium carterae*; or a fraction obtained from the extract.

In accordance with still another aspect of the present invention, there is provided a method for removing *mycoplasma* contamination from cells contaminated with *mycoplasma*, the method comprising (i) treating cells contaminated with *mycoplasma* with an enzyme solution for single cell-isolation to obtain a cell suspension; (ii) removing cell clumps from the cell suspension obtained from the step (i); and (iii) culturing the cell suspension obtained from the step (ii) or cells harvested from the cell suspension in a medium containing an agent having a *mycoplasma* inhibitory activity.

Advantageous Effects

It is newly found by the present invention that an extract of biomass obtained by culturing a strain, such as *Amphidinium kiebsii*, *Amphidinium carterae*, or the like, which is known as an algae inducing red tide, or a fraction obtained from the extract selectively induces *mycoplasma* death. In particular, the extract or fraction may prevent the *mycoplasma* contamination during cell culturing; and also, may remove the *mycoplasma* contamination from cells contaminated with *mycoplasma*, thereby being able to obtain normal cells. Accordingly, the cell culturing method according to the present invention makes it possible to stably perform culturing cells without *mycoplasma* contamination. And also, the method for removing *mycoplasma* contamination according to the present invention is usefully applied for obtaining normal cells from cells contaminated with *mycoplasma*.

In addition, it is newly found by the present invention that if cells contaminated with *mycoplasma* include cell clumps, an agent having a *mycoplasma* inhibitory activity cannot penetrate into the cell clumps. In particular, when sub-culturing, cells obtained by the treatment with an enzyme solution for single cell-isolation still include cell clumps even in low level, and thus the *mycoplasma* contamination inside cell clumps cannot be fundamentally prevented. Therefore, according to the present invention, *mycoplasma* contamination can be fundamentally prevented by additionally performing a step for removing cell clumps, after treating with an enzyme solution for single cell-isolation, in cell culture.

DESCRIPTION OF DRAWINGS

In FIG. 1, *Mycoplasma fermentans*-derived DNA (Minerva, Cat. No. 51-0117, Germany) was used as a positive control, and distilled water was used as a negative control.

In FIG. 2, M is a size marker, and *Mycoplasma fermentans*-derived DNA (Minerva, Cat. No. 51-0117, Germany) was used as a positive control.

In FIG. 5, *Mycoplasma fermentans*-derived DNA (Minerva, Cat. No. 51-0117, Germany) was used as a positive control, and distilled water was used as a negative control.

BEST MODE

Figure 1:
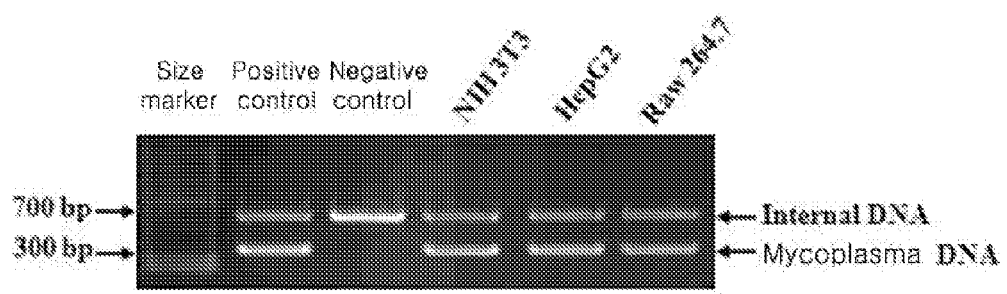
FIG. 1 shows electrophoresis images of cell lines NIH3T3, HepG2, and Raw 264.7 which were diagnosed as being contaminated with *mycoplasma* by using a *mycoplasma* diagnosis kit.

The phrase "an amphidinol-producing strain" used herein refers to a strain that is capable of producing polyene-polyhydroxy compounds known as amphidinols (AMs). Up to now, 15 species of AMs (AM1 to AM15) are known, and various analogues derived from these AMs are also referred to as AMs. Also, although only *Amphidinium klebsii* and *Amphidinium carterae*, which belong to Dinoflagellates, are known as a strain producing amphidinol, all of the recombinant strains and mutants having said ability (that is, amphidinol-producing potential) are understood as an amphidinol-producing strain. In addition, a strain producing amphidinol analogues, its recombinant strain, and its mutants are also understood as an amphidinol-producing strain.

The present invention provides a cell culturing method for preventing *mycoplasma* contamination, the cell culturing method comprising culturing cells in a medium that comprises an extract of biomass obtained by culturing an amphidinol-producing strain, preferably *Amphidinium klebsii* or *Amphidinium carterae*; or a fraction obtained from the extract.

The strains *Amphidinium klebsii* and *Amphidinium carterae* belonging to Dinoflagellates are known as an algae inducing red tide. Culturing, extracting of biomass, and fractionizing may be performed according to known methods, e.g., Gopal K. Paul et al., J. Mar. Biotechnology (1997) 5: 124-128; Toshihiro Houdai et al., Tetrahedron 57 (2001) 5551-5555; or Reiko Echigoya et al., Harmful algae 4 (2005) 383-389.

For example, the strain *Amphidinium klebsii* may be cultured in an incubator containing sea water under light, and a resulting biomass may be harvested by filtering with a glass filter.

Also, the extraction of biomass may be performed by extracting the obtained biomass sequentially with a $C_1$ to $C_4$ alcohol (for example, methanol) and acetone/water and ethyl acetate/n-butanol. Specifically, the extract may be obtained by performing an extraction process which comprises: (a) extracting the biomass with a $C_1$ to $C_4$ alcohol and acetone; (b) extracting the extract obtained from the step (a) with water and ethyl acetate, followed by separating an aqueous layer; and (c) extracting the aqueous layer obtained from the step (b) with n-butanol, followed by separating an n-butanol layer. In the step (a), the extraction may be performed using a mixed solvent of $C_1$ to $C_4$ alcohol and acetone. Alternatively, the extraction may be performed by extracting the biomass with $C_1$ to $C_4$ alcohol to obtain a first extract, extracting the remaining biomass with acetone to obtain a second extract, and then mixing the first and second extracts. The amounts of $C_1$ to $C_4$ alcohol and acetone are not limited, and for example, may be in a range of 10 to 300 times ml/g greater than the weight of the biomass. In the step (b), a weight ratio of water to ethyl acetate may be in a range of 1:2 to 1:5, and amounts thereof may be in a range of 10 to 50 times ml/g greater than the extract obtained from the step (a). In the step (c), the separated n-butanol layer obtained from the extraction with n-butanol may be dried according to conventional drying methods, e.g., drying under reduced pressure, to obtain the extract in the form of powder.

And also, the fractionizing may be performed according to known methods, e.g., Gopal K. Paul et al., J. Mar. Biotechnology (1997) 5: 124-128; Toshihiro Houdai et al., Tetrahedron 57 (2001) 5551-5555; or Reiko Echigoya et al., Harmful algae 4 (2005) 383-389. For example, the n-butanol extract is sequentially subjected to an HW-40 (Toyopearl, Tosoh) column chromatography using 50% methanol, sephadex LH-20 (Pharmacia-LKB) column chromatography using 100% methanol, and ODS (YMC, ODS-AQ) column chromatography using 0-50% acetonitrile, followed by reversed-phase HPLC using acetonitrile as a solvent. Through the fractionizing, the following polyene-polyhydroxy compounds (AM1 to AM15) known as amphidinols (AMs) may be obtained.

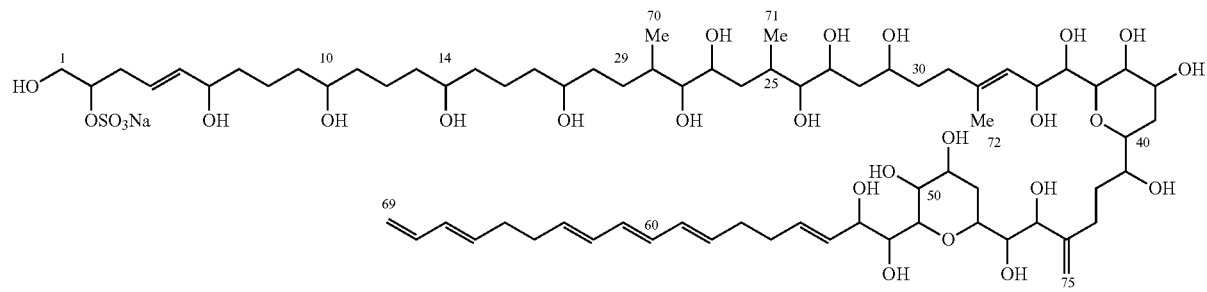
AM 1
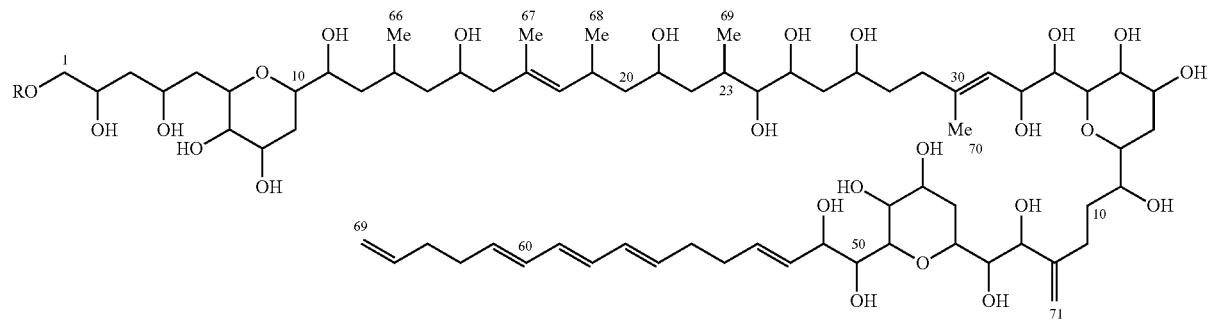
AM 2, R = H
AM 11, R = SO₃Na
AM 2 & AM 11
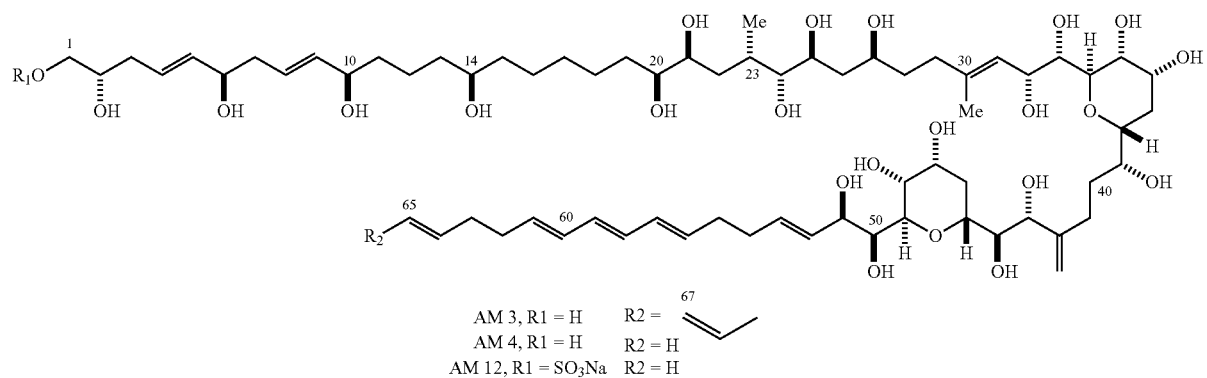
AM 3, R1 = H    R2 = 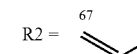
AM 4, R1 = H    R2 = H
AM 12, R1 = SO₃Na    R2 = H
AM 3, AM 4 & AM 12
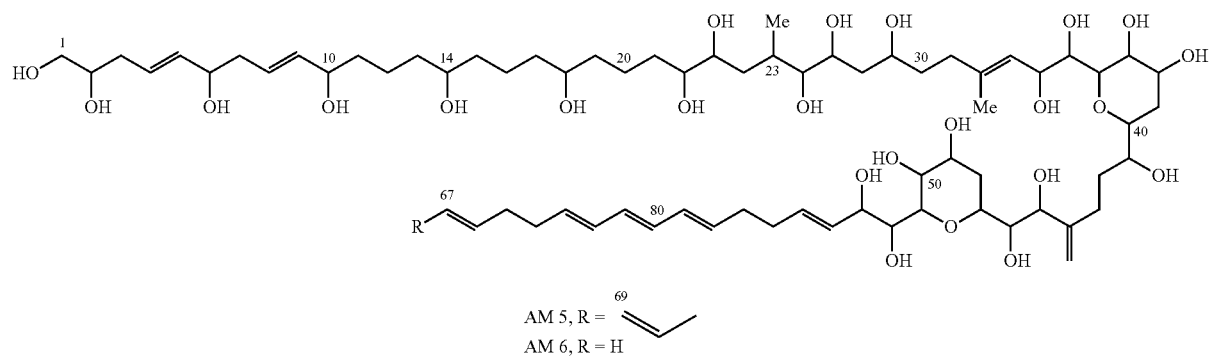
AM 5, R = (structure)
AM 6, R = H
AM 5 & AM 6

-continued

AM 7, AM 14 & AM 15

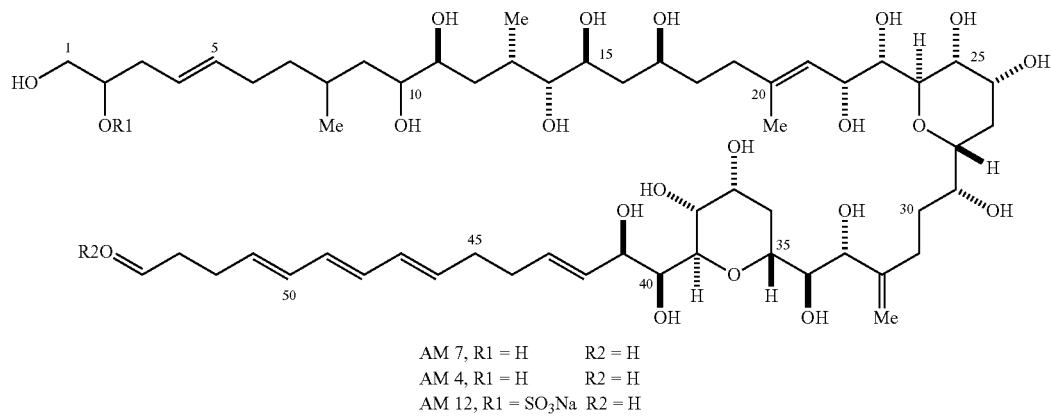

AM 7, R1 = H    R2 = H
AM 4, R1 = H    R2 = H
AM 12, R1 = SO₃Na  R2 = H

AM 9 & AM 13

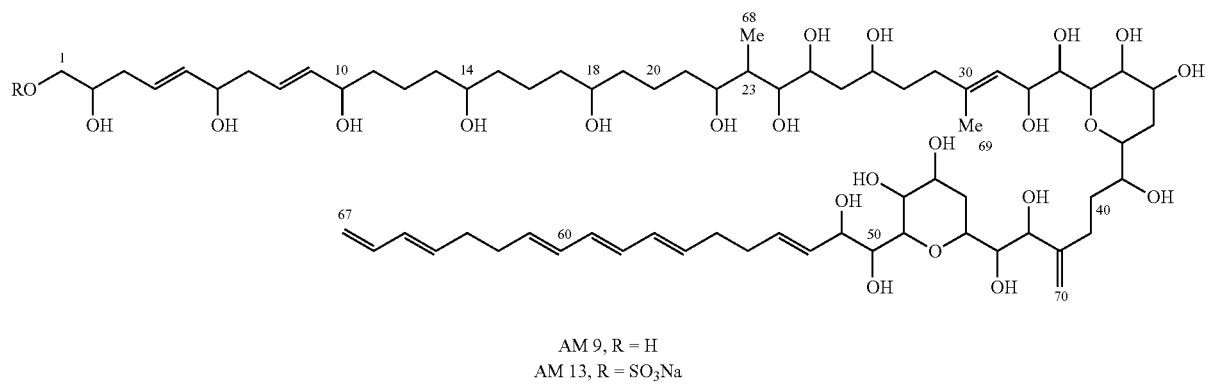

AM 9, R = H
AM 13, R = SO₃Na

AM 10

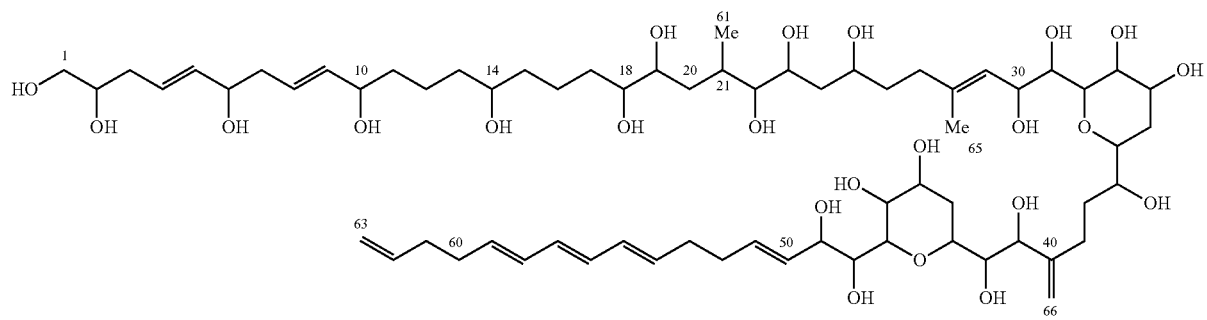

It is newly found by the present invention that the compounds of amphidinol 1 (AM1), amphidinol 2 (AM2), amphidinol 3 (AM3), amphidinol 4 (AM4), amphidinol 5 (AM5), amphidinol 6 (AM6), amphidinol 7 (AM7), and amphidinol 9 (AM9) among the fractions, especially the compound of amphidinol 3 (AM3), have excellent activity through selectively inducing *mycoplasma* death. AM1, AM2, AM3, AM4, AM5, AM6, AM7, and AM9 have the following chemical structures represented by Formulae 1 to 8 below.

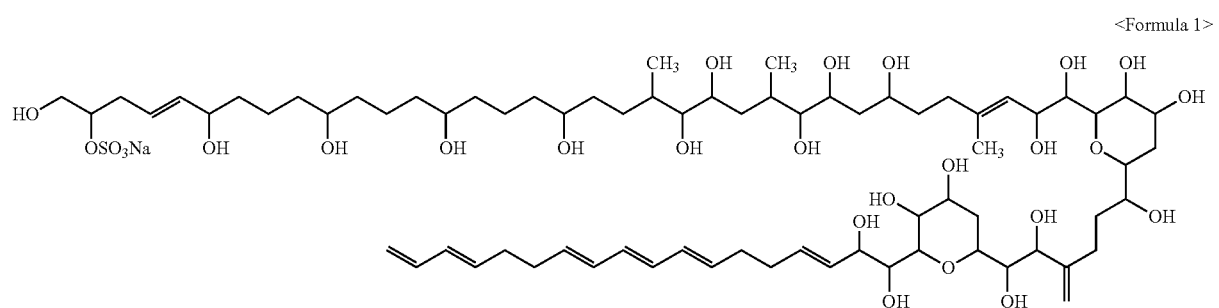
<Formula 1>
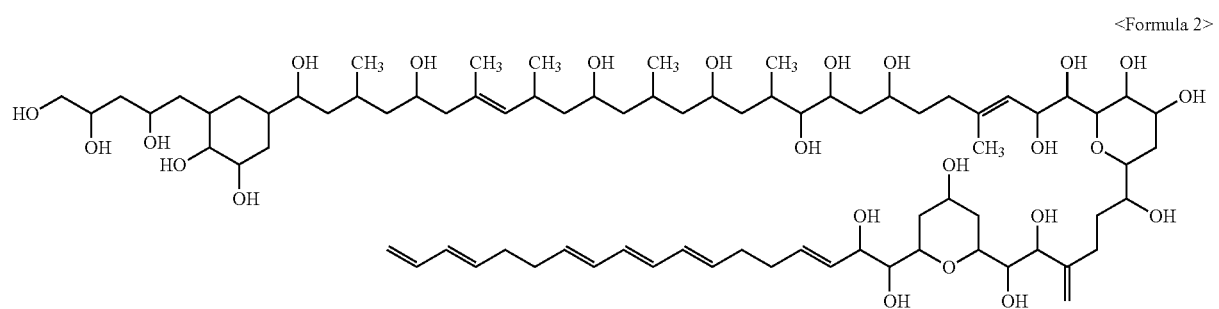
<Formula 2>
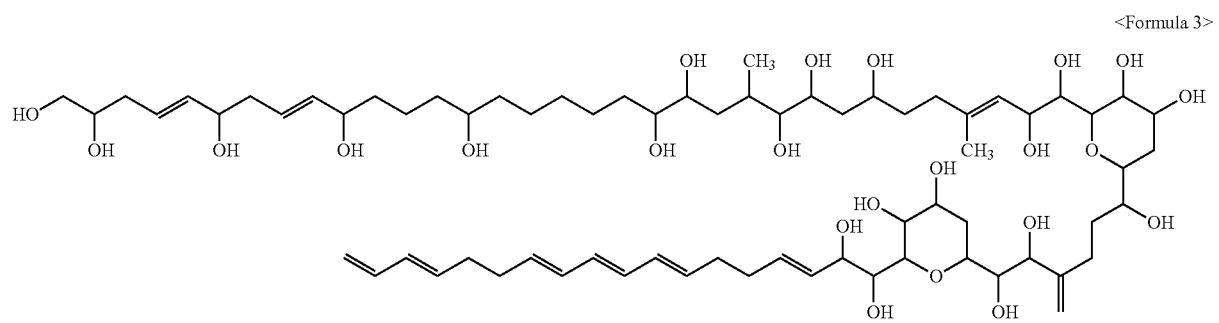
<Formula 3>
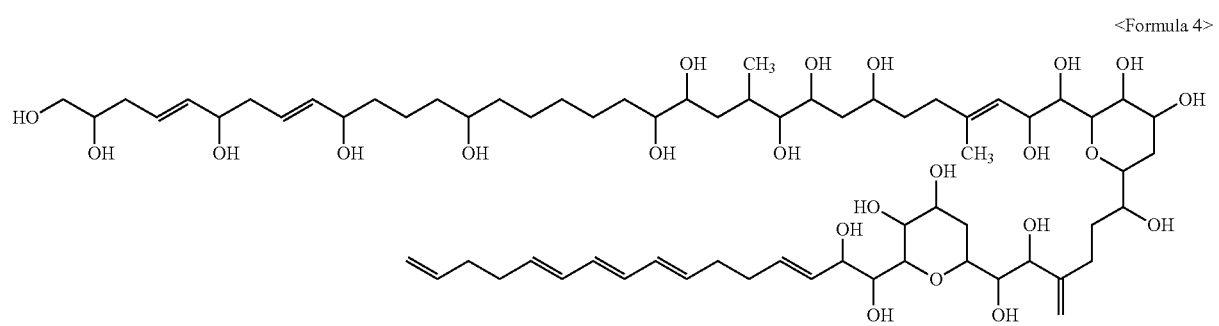
<Formula 4>
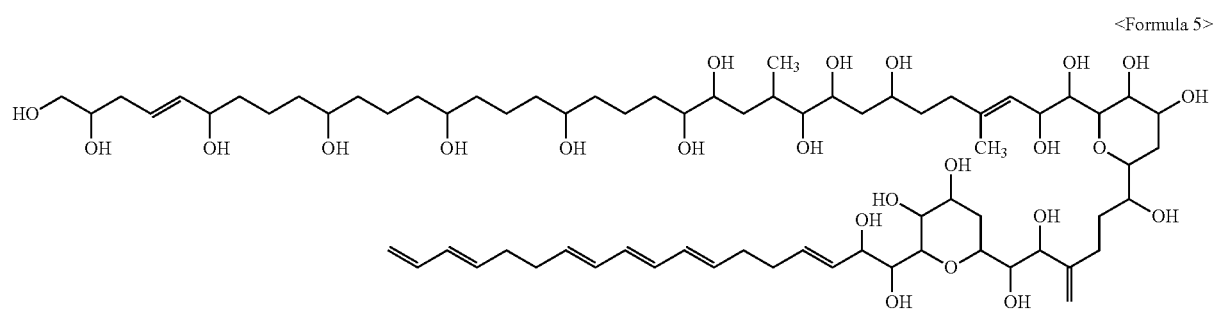
<Formula 5>

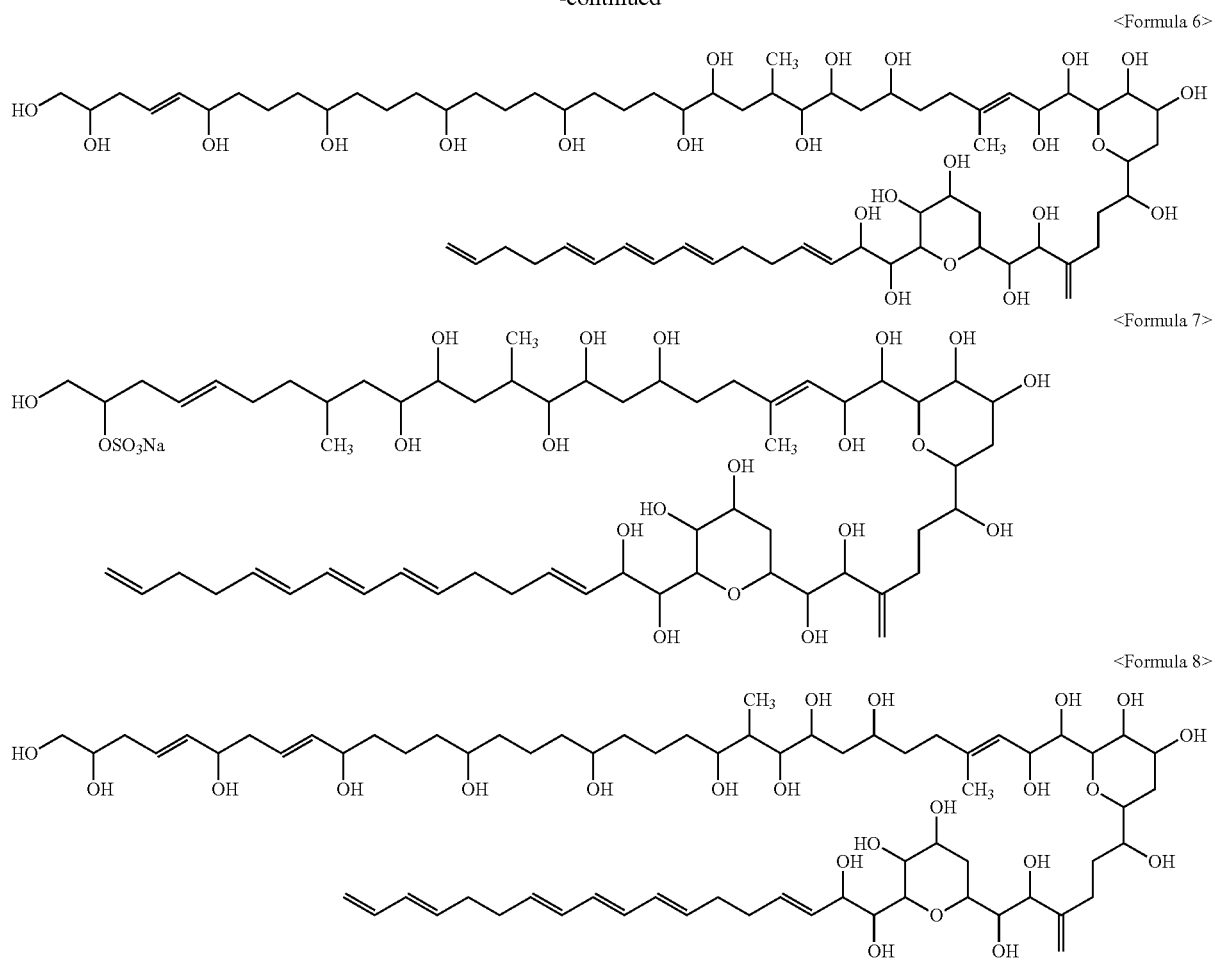

In the cell culturing method for preventing *mycoplasma* contamination according to the present invention, cells available herein are cells that are known to likely be contaminated with *mycoplasma*, and non-limiting examples of such cells are NIH3T3 cell line, HepG2 cell line, Raw 264.7 cell line, and the like. A medium available herein may be any of various media that are known to be suitable for cells that are to be cultured.

In the cell culturing method for preventing *mycoplasma* contamination, a concentration of the extract or fraction in the medium may be in a range of 0.1 nM to 100 μM, preferably 1 nM to 1 μM, more preferably 5 nM to 100 μM.

And also, the medium may further include, in addition to the extract or fraction, an antibiotic or lipopeptide that is known to have *mycoplasma* inhibitory activity. For example the medium may further include an antibiotic, such as ciprofloxacin, doxycycline, rifampicin, chloramphenicol, plasmocin, clindamycin, azithromycin, clarithromycin, tetracycline, tiamulin, or the like; or a lipopeptide, such as surfactin, alamethicin, cecropin P1, globomycin, gramicidin S, magainin 2, melitin, polymixin B, tylosin, valinomycin, or the like. According to an embodiment of the present invention, the medium may further comprise 1 to 50 μM of surfactin, 0.1 to 100 μg/ml of ciprofloxacin, or 0.1 to 100 μg/ml of rifampicin.

The present invention also provides a method for removing *mycoplasma* contamination from cells contaminated with *mycoplasma*, the method comprising culturing cells contaminated with *mycoplasma* in a medium that comprises an extract of biomass obtained by culturing an amphidinol-producing strain; or a fraction obtained from the extract.

In the method for removing *mycoplasma* contamination from cells contaminated with *mycoplasma* according to the present invention, the cells contaminated with *mycoplasma* may be any cells that are contaminated with *mycoplasma*, for example, NIH3T3 cell line, HepG2 cell line, or Raw 264.7 cell line which are contaminated with *mycoplasma*, but are not limited thereto. Examples of the cells contaminated with *mycoplasma* are a cell contaminated with *mycoplasma* which is obtained by typical culturing; a cell contaminated with *mycoplasma* which is about to be sub-cultured or is being sub-cultured; and a cell contaminated with *mycoplasma* which is completely sub-cultured and is about to be used in experiments. For example, the method according to the present invention may be applied to the cells contaminated with *mycoplasma* which is about to be sub-cultured or is being sub-cultured. The cell contaminated with *mycoplasma* may be prepared by removing a medium and washing once or twice with e.g., a phosphate buffer. The medium may be any one of various media that are known to be suitable for a contaminated cell (that is, a cell infected with *mycoplasma*) to be cultured.

In the method for removing *mycoplasma* contamination from cells contaminated with *mycoplasma* according to the present invention, a concentration of the extract or fraction in the medium may be in a range of 0.1 nM to 100 µM, preferably 1 nM to 1 µM, more preferably 5 nM to 100 nM.

And also, the medium may further include, in addition to the extract or fraction, an antibiotic or lipopeptide that is known to have *mycoplasma* inhibitory activity. For example the medium may further include an antibiotic, such as ciprofloxacin, doxycycline, rifampicin, chloramphenicol, plasmocin, clindamycin, azithromycin, clarithromycin, tetracycline, tiamulin, or the like; or a lipopeptide, such as surfactin, alamethicin, cecropin P1, globomycin, gramicidin S, magainin 2, melitin, polymixin B, tylosin, valinomycin, or the like. According to an embodiment of the present invention, the medium may further comprise 1 to 50 µM of surfactin, 0.1 to 100 µg/ml of ciprofloxacin, or 0.1 to 100 µg/ml of rifampicin.

Culturing of the cells contaminated with *mycoplasma*, that is, the treatment of the cells contaminated with *mycoplasma* with the extract or fraction may be performed by, for example, performing cultivation for a typical cell culture time, and if necessary, the culturing may be performed by sub-culturing the cells in a medium including the extract or fraction. In the case of cells cultured as described above, *mycoplasma* is not further detected and is effectively removed, thereby enabling production of normal cells that are not infected with *mycoplasma*

It is newly found by the present invention that if cells contaminated with *mycoplasma* include cell clumps, an agent having a *mycoplasma* inhibitory activity cannot penetrate into the cell clumps. In particular, when sub-culturing, cells obtained by the treatment with an enzyme solution for single cell-isolation still include cell clumps even in low level, and thus the *mycoplasma* contamination inside cell clumps cannot be fundamentally prevented. Therefore, according to the present invention, *mycoplasma* contamination can be fundamentally prevented by additionally performing a step for removing cell clumps, after treating with an enzyme solution for single cell-isolation, in cell culture.

That is, in accordance with another aspect of the present invention, there is provided a method for removing *mycoplasma* contamination from cells contaminated with *mycoplasma*, the method comprising (i) treating cells contaminated with *mycoplasma* with an enzyme solution for single cell-isolation to obtain a cell suspension; (ii) removing cell clumps from the cell suspension obtained from the step (i); and (iii) culturing the cell suspension obtained from the step (ii) or cells harvested from the cell suspension in a medium containing an agent having a *mycoplasma* inhibitory activity.

The method according to the present invention including the step for removing cell clumps includes treating cells contaminated with *mycoplasma* with an enzyme solution for single cell-isolation to obtain a cell suspension [that is, the step (i)].

The cells contaminated with *mycoplasma* may be any cells that are contaminated with *mycoplasma*, for example, NIH3T3 cell line, HepG2 cell line, or Raw 264.7 cell line which are contaminated with *mycoplasma*, but are not limited thereto. Examples of the cells contaminated with *mycoplasma* are a cell contaminated with *mycoplasma* which is obtained by typical culturing; a cell contaminated with *mycoplasma* which is about to be sub-cultured or is being sub-cultured; and a cell contaminated with *mycoplasma* which is completely sub-cultured and is about to be used in experiments. For example, the method according to the present invention may be applied to the cells contaminated with *mycoplasma* which is about to be sub-cultured or is being sub-cultured. For the subsequent enzyme solution treatment, the cell contaminated with *mycoplasma* may be prepared by removing a medium and washing once or twice with e.g., a phosphate buffer.

The enzyme solution for single cell-isolation may be any one of various enzymatic solutions that are used to detach cells that are fixedly grown on a culture plate (for example, a culture plate, a culture flask, or an incubator) into the form of single cells. For example, the enzyme solution for single cell-isolation may be a solution comprising trypsin and ethylenediaminetetraacetic acid (typically referred to as "trypsin-EDTA solution"). Also, the enzyme solution for single cell-isolation may include, for example, a protease and collagenase which are used in a typical cell detachment solution for detaching cells from a culture plate. Preferably, a solution comprising trypsin and EDTA may be used, and a weight ratio of trypsin to EDTA may be about 25:1, and concentrations thereof (for example, a concentration in a phosphate buffer solution) are, respectively, 0.025% and 0.001%, but are not limited thereto. And also, a commercially available reagent such as Trypsin/EDTA Solution (Invitrogen, Cat. No. R-001-100) may be used as a trypsin-EDTA solution. The enzyme solution for single cell-isolation, including the trypsin-EDTA solution, may be used in an amount typically used in the field of cell culture.

The enzyme solution treatment may be performed by adding an enzyme solution for single cell-isolation to cells (for example, cells obtained by washing with a phosphate buffer to remove a medium), incubating the mixture at a temperature of about 37° C. for about 10 minutes, adding a DMEM medium or the like to the mixture to obtain a cell suspension, and then centrifuging the cell suspension to remove a supernatant. A medium for culturing cells, such as a DMEM medium, may be added to the resulting cells to obtain a cell suspension.

The method according to the present invention including the step for removing cell clumps includes removing cell clumps from the cell suspension obtained from the step (i) [that is, the step (ii)].

The cell clump removal method may be any one of various methods that can be used to remove cell clumps. For example, cell clumps may be removed by filtering using a filter having an appropriate pore size. According to an embodiment of the present invention, the step (ii) may be performed by filtering the cell suspension obtained from the step (i) through a filter having a pore size of 10 to 100 µm, preferably 30 to 70 µm, more preferably about 40 µm to remove cell clumps.

The method according to the present invention including the step for removing cell clumps includes culturing the cell suspension obtained from the step (ii) or cells harvested from the cell suspension in a medium containing an agent having a *mycoplasma* inhibitory activity [that is, the step (iii)].

The cell suspension obtained from the step (ii) may be controlled to have an cell concentration suitable for culturing by using a medium. Also, the harvesting of cells from the cell suspension obtained from the step (ii) may be performed by using a typical method, such as a centrifuging method. And also, the medium used in the step (iii) may be any one of various media that are known to be suitable for a cell to be cultured, and if necessary, the medium may be supplemented with a cytokine such as FBS.

A method according to the present invention may be performed by repeatedly conducting the step (i) to the step (iii). For example, the step (i) to the step (iii) may be repeatedly performed twice or four times.

The agent having a *mycoplasma* inhibitory activity may be any one of various materials that are used to inhibit *mycoplasma*. Examples thereof are an antibiotic, peptide, or lipopeptide such as 6-methylpurine deoxyriboside, 6-methylpurin riboside, ciprofloxacin, doxycycline, rifampicin, chloramphenicol, plasmocin, clindamycin, azithromycin, clarithromycine, tetracycline, tiamulin, surfactin, alamethicin, cecropin P1, globomycin, gramicidine S, magainin 2, melittin, polymyxin B, tylosin, and valinomycin. An amount of the antibiotic or lipopeptide (or peptide) for use herein may be appropriately determined according to known literatures. And also, a commercially available reagent for removing *mycoplasma*, for example, LookOut *Mycoplasma* Elimination Reagent (Sigma-Aldrich), BM-cyclin (Roche), or the like, may be used.

Preferably, the agent having a *mycoplasma* inhibitory activity may be an extract of biomass obtained by culturing an amphidinol-producing strain; or a fraction obtained from the extract. The amphidinol-producing strain, the extract of biomass, and the fraction are the same as described above.

As described above, amphidinol 1 (AM1), amphidinol 2 (AM2), amphidinol 3 (AM3), amphidinol 4 (AM4), amphidinol 5 (AM5), amphidinol 6 (AM6), amphidinol 7 (AM7), and amphidinol 9 (AM9) are preferable among the fractions. Amphidinol 3 (AM3) is more preferable.

A concentration of the extract or fraction in the medium may be in a range of 0.1 nM to 100 μM, preferably 1 nM to 1 μM, more preferably 5 nM to 100 nM.

The present invention will be described in further detail with reference to the following examples. These examples are for illustrative purposes only and are not intended to limit the scope of the present invention.

EXAMPLE 1

Isolation of Amphidinol Derivatives

Amphidinol derivatives were isolated from *Amphidinium klebsii* according to the disclosure made by Gopal K. Paul et al (Gopal K. Paul et al., J. Mar. Biotechnology (1997) 5: 124-128). *Amphidinium klebsii* was cultured in three 5 liter-incubators each including 2 liters of sea water at a temperature of 24° C. under light with a brightness of 16 lux for 4 weeks, followed by filtering with a glass filter to harvest algae biomass. 25 g of the algae biomass was extracted with 1 liter of methanol three times. Thereafter, the algae biomass was further extracted three times with 300 ml of acetone. These extracts were mixed and then a volatile solution was removed therefrom with an evaporator (rotary vacuum evaporator, Buchi R-205, Flawil, Switzerland). Then, 400 ml of a mixed solution of water and ethyl acetate (1:4, v/v) was added to the remaining non-volatile layer, and then an aqueous layer was separated. The aqueous layer was extracted with n-butanol and then the resulting n-butanol layer was separated. A portion of the n-butanol layer was dried under reduced pressure to obtain powder (hereinafter referred to as "butanol extract"), and the remaining n-butanol layer was used for the following fractionizing process.

The remaining n-butanol layer was subjected to column chromatography by sequentially with an HW-40 (Toyopearl, Tosoh) column using 50% methanol, a sephadex LH-20 (Pharmacia-LKB) column using 100% methanol as a solvent, and an ODS (YMC, ODS-AQ) column using 0-50% acetonitrile as a solvent. Finally, a reversed-phase HPLC was performed thereon by using 33% acetonitrile as a solvent to isolate amphidinol derivatives (that is, AM1-AM15). According to the Leo A. Paquette method (Org. Lett., 2005, 7 (14), pp 3111-3114), H-NMR and $^1$H-$^1$H COSY were measured at a frequency of 500 MHz, using DMSO-$d_6$ as a solvent, to analyze the obtained amphidinol derivatives.

EXAMPLE 2

Evaluation on Effects of Amphidinol Derivatives on *Mycoplasma*

In order to evaluate the effects of the extract and amphidinol derivatives prepared in Example 1 on *mycoplasma*, *Mycoplasma hyorhinis* (ATCC17981) was cultured in a PPLO medium (pleuropneumonia-like organism basal medium, Difco Laboratories, Detroit, USA) supplemented with a fetal calf serum and a yeast extract, according to the method disclosed by Hayflick (Hayflick, 1965, Tex. Rep. Bio. Med. 23, 285-303). That is, 100 μl of the medium was placed on each well of a 96-well plate, and a sample (that is, the extract and amphidinol derivatives prepared in Example 1) was added to each well, such that each sample was diluted from 2 times (i.e., 2× diluted) to 12 times (i.e., 12× diluted), the starting concentration being 1 mg/ml. *mycoplasma* was cultured in a PPLO medium (pleuropneumonia-like organism basal medium, Difco Laboratories, Detroit, USA) supplemented with a fetal calf serum and a yeast extract, at a temperature of 37° C. for 48 hours. The resulting culture medium was diluted with the PPLO medium at a ratio of 1:10. 100 μl of the diluted culture medium was added to each well of the 96-well plate, so that the total amount of each well was 200 μl. After culturing at a temperature of 37° C. for 24 hours, 40 μl of 0.2 mg/ml INT (p-iodonitrotetrazolium) was added thereto and culturing was further performed for 4 hours. If the medium turns pink following the culturing, the color change means that metabolism of *mycoplasma* actively occurs. Also, if *mycoplasma* is suppressed by the sample, the medium turned pink less. Accordingly, a 50% inhibition concentration (IC50) was obtained by measuring a final concentration at which color change did not occur. Results thereof are as shown in Table 1.

TABLE 1

| Test compounds | IC50 |
|---|---|
| DMSO | − |
| AM1 | +++ |
| AM2 | +++ |
| AM3 | ++++ |
| AM4 | +++ |
| AM5 | +++ |
| AM6 | +++ |
| AM7 | +++ |
| AM9 | +++ |
| AM10 | ++ |
| AM11 | ++ |
| AM12 | ++ |
| AM13 | ++ |
| AM14 | ++ |
| AM15 | ++ |
| Butanol extract | +++ |

−: No inhibition
++: 10~100 μg/ml
+++: 1~20 μg/ml
++++: 0.25 μg/ml~10 μg/ml

From the results shown in Table 1, it can be seen that the amphidinol derivatives have an inhibitory activity against *mycoplasma*. Especially, AM3 (compound of Formula 3) showed excellent inhibitory activity against *mycoplasma* at a concentration of about 0.25 μg/ml.

EXAMPLE 3

Removal of *mycoplasma* from Cell Lines Contaminated with *Mycoplasma*

(1) Collecting Cell Lines Contaminated with *Mycoplasma*

Various cell lines constructed in laboratories of colleges located in Seoul were obtained. The obtained cell lines were cultured in a DMEM (GIBCO BRL, Cat. No. 12800-058) for 3 days, and then the cells were harvested. PCR was performed thereon with a *mycoplasma* diagnosis kit (Promokine, Germany; Cellsafe Co., Ltd., Korea) according to the enclosed protocol. The resulting PCR products were electrophoresed on a 1% agarose gel to measure the *mycoplasma* contamination. As a result, it was confirmed that three cell strains, i.e., NIH3T3, HepG2, Raw 264.7 cell lines, were infected with *mycoplasma* (see FIG. 1).

The cell lines NIH3T3, HepG2, and Raw 264.7, which were confirmed to be contaminated with *mycoplasma*, were each inoculated at a concentration of $1\times10^6$ cells on a T-75 culture flask (NUNC, Cat. No. 156367). DMEM (GIBCO BRL, Cat. No. 12800-058) containing 10% or less of serum (GIBCO BRL, Cat. No. 10082-147) was added thereto, followed by culturing for 3 days.

(2) Removing *Mycoplasma* from Cell Lines Contaminated with *Mycoplasma*

Figure 2:
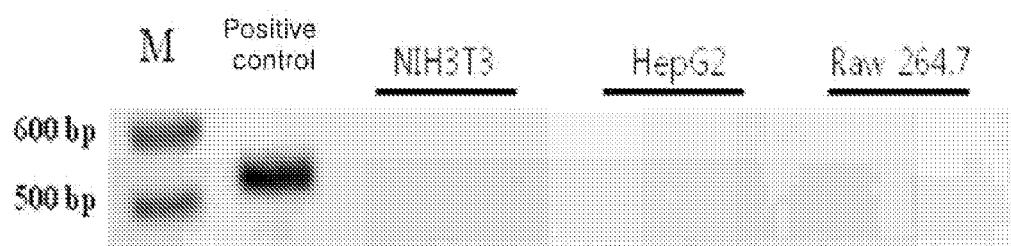
FIG. 2 shows measurement results of *mycoplasma* contamination removal activities of amphidinol 3 (AM3) on cell lines contaminated with *mycoplasma*.

The cell lines NIH3T3, HepG2, and Raw 264.7, which were confirmed to be contaminated with *mycoplasma*, were each inoculated at a concentration of $1\times10^5$ cells on a T-75 culture flask (NUNC, Cat. No. 156367). DMEM (GIBCO BRL, Cat. No. 12800-058) containing 10% or less of serum (GIBCO BRL, Cat. No. 10082-147) was added thereto and then 20 μg/ml of amphidinol 3 (AM3) was added thereto. After culturing for 3 days, the obtained cells were treated with Trypsin-EDTA to obtain a cell solution. The resulting cells ($1\times10^5$ cells) which was treated with amphidinol 3 (AM3) were inoculated. DMEM (GIBCO BRL, Cat. No. 12800-058) containing 10% or less of serum (GIBCO BRL, Cat. No. 10082-147) was added thereto and then 20 μg/ml of amphidinol 3 (AM3) was added thereto. After culturing for 3 days, the cells were harvested. PCR was performed thereon with a *mycoplasma* diagnosis kit (Promokine, Germany; Cellsafe Co., Ltd., Korea) according to the enclosed protocol. The resulting PCR products were electrophoresed on a 1% agarose gel to measure the *mycoplasma* contamination. Results thereof are as shown in FIG. 2. From the results shown in FIG. 2, it can be seen that *mycoplasma* was completely removed from all of the cell lines treated with amphidinol 3 (AM3).

(3) Co-Treatment with Amphidinol 3 (AM3) and Cyclic Lipopeptide/Antibiotic

Figure 3:
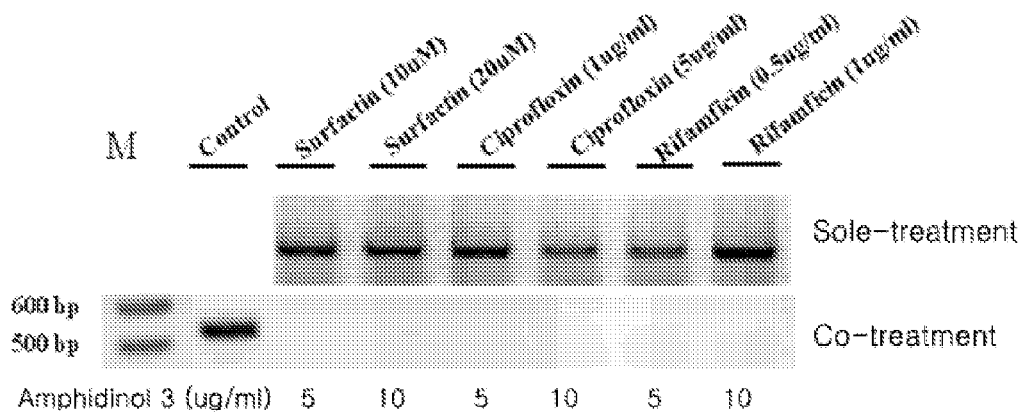
FIG. 3 shows measurement results of *mycoplasma* contamination removal activities when cell lines contaminated with *mycoplasma* were treated with surfactin, ciprofloxacin, or rifampicin alone or together with amphidinol 3 (AM3).

*Mycoplasma* contamination was measured in the same manner as in (2) except that HepG2 was used as a cell line contaminated with *mycoplasma*; and instead of the treatment with amphidinol 3 (AM3), 5 μg/ml and 10 μg/ml of amphidinol 3 (AM3) was used together with surfactin (10 μM or 20 μM), ciprofloxacin (1 μg/ml or 5 μg/ml), or rifampicin (0.5 μg/ml or 1 μg/ml). Results thereof are shown in FIG. 3. From the results shown in FIG. 3, it can be seen that when surfactin, ciprofloxacin, or rifampicin was used alone, the *mycoplasma* contamination remained. However, when surfactin, ciprofloxacin, or rifampicin was used together with amphidinol 3 (AM3), the *mycoplasma* contamination was completely removed.

EXAMPLE 4

Figure 4:
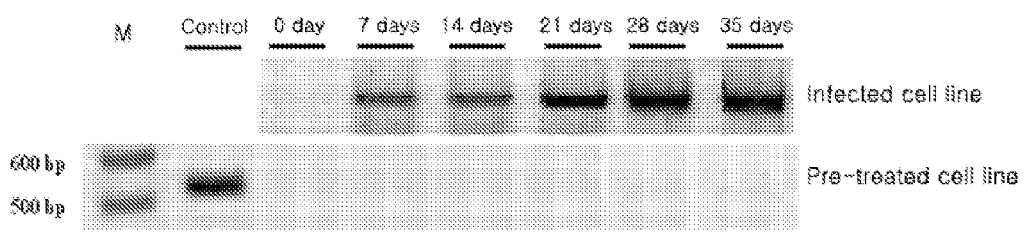
FIG. 4 shows evaluation results of preventive activity against *mycoplasma* contamination during cell culturing.

Evaluation of Preventive Activity Against *Mycoplasma* Contamination During Cell Culturing A cell line HepG2, which was not contaminated with *mycoplasma*, was inoculated at a concentration of $1\times10^5$ cells on DMEM (GIBCO BRL, Cat. No. 12800-058) including 10% or less serum (GIBCO BRL, Cat. No. 10082-147). The cell line was treated with 20 μg/ml of amphidinol 3 (AM3) and 20 μM of surfactin, followed by inoculation of $1\times10^3$ cfu (colony formin unit) of *Mycoplasma hyorhinis* (ATCC 17981). The cell line was cultured in an incubator at a temperature of 37° C. and in a condition of 5% $CO_2$ for 3 days. Sub-culturing was performed twice per week. The cells were harvested every week and then PCR was performed thereon with a *mycoplasma* diagnosis kit (Promokine, Germany; Cellsafe Co., Ltd., Korea) according to the enclosed protocol. The resulting PCR products were electrophoresed on a 1% agarose gel to measure the *mycoplasma* contamination. Results thereof are as shown in FIG. 4. From the results shown in FIG. 4, it can be seen that, even when *mycoplasma* contamination was artificially induced, the obtained cells were stably cultured without *mycoplasma* contamination.

EXAMPLE 5

Evaluation of *Mycoplasma* Removal Potential According to Cell Clumps Removal (1) Evaluation of *Mycoplasma* Removal Potential on Sub-Culturing after Filtering A medium was removed from the cell culture (80 to 90% confluent) which was cultured in the T-75 culture flask in (1) of Example 3 and which was confirmed as being contaminated with *mycoplasma*. The obtained cells were washed twice with 10 ml of a phosphate buffer solution. 2 ml of trypsin-EDTA was added thereto, followed by incubating at a temperature of 37° C. for 10 minutes to detach cells. Then, DMEM (GIBCO BRL, Cat. No. 12800-058) was added thereto to obtain 10 ml of cell suspension, which was then transferred to a 15 ml conical tube. The cell suspension in the conical tube was centrifuged at a rate of 1,500 rpm for 5 minutes, and then the supernatant was removed therefrom. 10 ml of 5% FBS-containing DMEM (GIBCO BRL, Cat. No. 12800-058) was added to the conical tube to obtain a cell suspension. The obtained cell suspension was divided into two groups each having an amount of 5 ml. The cell suspension of the group 1 was passed through a filter having a pore size of 40 μm, while the suspension of the group 2 was not filtered. The cell suspensions of the group 1 and 2 were diluted with 5% FBS-including DMEM (GIBCO BRL, Cat. No. 12800-058) to adjust the cell concentration to about $2.5\times10^5$ cells/ml, respectively. 4 nil of each cell suspension of the group 1 and 2 (each having about $2.5\times10^5$ cells/ml of cells) was transferred to a 15 ml tube, and then 5.5 ml of 5% FBS-containing DMEM (GIBCO BRL, Cat. No. 12800-058) was added thereto. The mixture was treated with 500 μl of *Mycoplasma* Elimination Reagent—initial treatment reagent (Sigma-Aldrich, Cat. no. M4569). 10 ml of each of the obtained mixtures was transferred to a T-75 culture flask, followed by culturing for 3 days in a $CO_2$ incubator for 3 days (passage 1 sub-culturing).

The medium was removed from the cell culture (80 to 90% confluent) which was cultured in the T-75 culture flask for 3 days. The obtained cells were washed twice with 10 ml of a phosphate buffer solution. 2 ml of trypsin-EDTA was added thereto, followed by incubating at a temperature of 37° C. for 10 minutes to detach the cells. Then, DMEM (GIBCO BRL, Cat. No. 12800-058) was added thereto to obtain 10 ml of cell suspension, which was then transferred to a 15 ml conical tube. The cell suspension in the conical tube was centrifuged at a rate of 1,500 rpm for 5 minutes, and then the supernatant was removed therefrom. 10 ml of 10% FBS-containing DMEM (GIBCO BRL, Cat. No. 12800-058) was added to the conical tube to obtain a cell suspension. The obtained cell suspension was divided into two groups each having an amount of 5 ml. As described above, the cell suspension of the group 1 was passed through a filter having a pore size of 40 µm, while the suspension of the group 2 was not filtered. The cell suspensions of the group 1 and 2 were diluted with 10% FBS-including DMEM (GIBCO BRL, Cat. No. 12800-058) to adjust the cell concentration to about $2.5 \times 10^5$ cells/ml, respectively. 4 ml of each cell suspension of the group 1 and 2 (each having about $2.5 \times 10^5$ cells/ml of cells) was transferred to a 15 ml tube, and then 5.5 ml of 10% FBS-containing DMEM (GIBCO BRL, Cat. No. 12800-058) was added thereto. The mixture was treated with 500 µl of *Mycoplasma* Elimination Reagent—initial treatment reagent (Sigma-Aldrich, Cat. no. M4569). 10 ml of each of the obtained mixtures was transferred to a T-75 culture flask, followed by culturing for 3 days in a $CO_2$ incubator for 2 days (passage 2 sub-culturing). The sub-culturing was performed twice more, and thus, passage 4 sub-culturing steps in total were performed.

Figure 5:
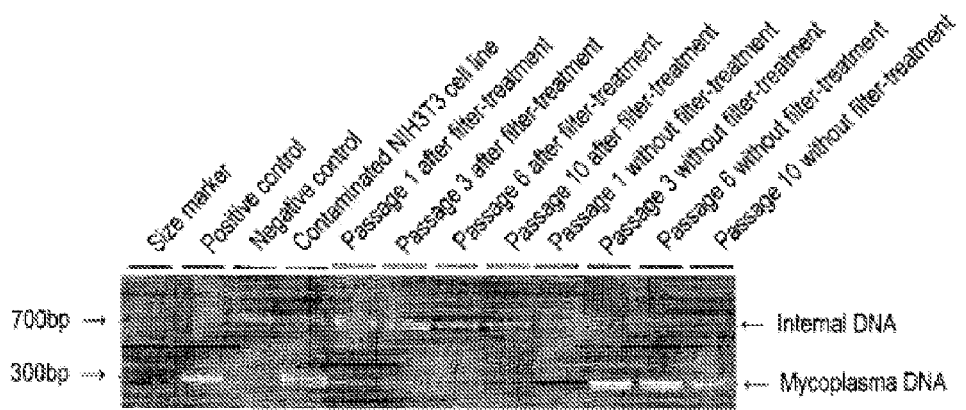
FIG. 5 shows electrophoresis images of the cells sub-cultured to passages 1, 3, 6, and 10 which were subjected to the *mycoplasma* contamination removal treatment in the presence or absence of cell clump removal step.

The cells sub-cultured to passage 4 were additionally sub-cultured to from is passage 1 to passage 33, and the respective sub-cultivations were performed according to a conventional cell culturing method, that is by treating with a trypsin-EDTA solution without the filtering and then culturing in a medium that did not contain a reagent for removing *mycoplasma*. *Mycoplasma* contamination was measured regarding the respective cells of the additional passages 1, 3, 6, 10, 12, 15, and 33 after the initial passage 4 treatments. Whether *mycoplasma* was removed was measured with a *mycoplasma* diagnosis kit (Promokine, Germany; Cellsafe Co., Ltd., Korea) according to the enclosed protocol. The resulting PCR products were electrophoresed on a 1% agarose gel to measure the *mycoplasma* contamination. Results thereof are as shown in Table 2. And also, FIG. 5 shows electrophoresis images obtained from the NIH3T3 cells of the group 1 and 2, which were sub-cultured to the additional passages 1, 3, 6, and 10.

TABLE 2

| | Passing through filter | | | No passing through filter | | |
|---|---|---|---|---|---|---|
| | NIH3T3 | HepG2 | Raw 264.7 | NIH3T3 | HepG2 | Raw 264.7 |
| Passage 1 after treatment | − | − | − | − | − | − |
| Passage 3 after treatment | − | − | − | + | + | + |
| Passage 6 after treatment | − | − | − | + | + | + |
| Passage 10 after treatment | − | − | − | + | + | + |
| Passage 12 after treatment | − | − | − | + | + | + |
| Passage 15 after treatment | − | − | − | + | + | + |
| Passage 33 after treatment | − | − | − | + | + | + |

* −: contamination removed, +: contamination

From the results shown in Table 2, it can be seen that, when filtering was performed, the *mycoplasma* contamination was completely removed from all of the cell lines. However, from the results shown in Table 2 and FIG. 5, it can be confirmed that when the step for removing cell clumps was not performed, *mycoplasma* DNA emerged from the cells sub-cultured to passage 3.

(2) Evaluation on *Mycoplasma* Removal Potential According to Pore Size

Sub-culturing was performed in the same manner as in (1), except that instead of the filters having a pore size of 40 µm, the filters (Millipore) having pore sizes of 11, 20, 30, 60, 80, 90, and 100 µm and the filters (Falcon) having pore sizes of 50 and 70 µm were used, and then the *mycoplasma* contamination was measured. Results thereof are shown in Table 3 below.

TABLE 3

| | Pore size (µm) | | | | | | | | |
|---|---|---|---|---|---|---|---|---|---|
| | 11 | 20 | 30 | 50 | 60 | 70 | 80 | 90 | 100 |
| Passage 1 after treatment | − | − | − | − | − | − | − | − | − |
| Passage 3 after treatment | − | − | − | − | − | − | − | − | − |
| Passage 6 after treatment | − | − | − | − | − | − | − | − | − |
| Passage 10 after treatment | − | − | − | − | − | − | − | − | − |
| Passage 12 after treatment | − | − | − | − | − | − | − | − | − |
| Passage 15 after treatment | − | − | − | − | − | − | − | − | − |
| Passage 33 after treatment | − | − | − | − | − | − | − | − | − |

* −: contamination removed, +: contamination

From the results shown in Table 3, it can be seen that when a filter having a pore size of 10 to 100 µm is used, the *mycoplasma* contamination can be completely removed.

(4) Evaluation on *Mycoplasma* Removal Potential when Amphidinol Derivative was Used Sub-culturing was performed in the same manner as in (1), except that 2 µg/ml of the compound of Formula 3 was used as a reagent for removing *mycoplasma*, and the filters (Millipore) having pore sizes of 11, 20, 30, 60, 80, 90, and 100 µm and the filters (Falcon) having pore sizes of 40, 50, and 70 µm were used, and then, the *mycoplasma* contamination was measured. Results thereof are shown Table 4 below.

TABLE 4

| | Pore size (µm) | | | | | | | | | |
|---|---|---|---|---|---|---|---|---|---|---|
| | 11 | 20 | 30 | 40 | 50 | 60 | 70 | 80 | 90 | 100 |
| Passage 1 after treatment | − | − | − | − | − | − | − | − | − | − |
| Passage 3 after treatment | − | − | − | − | − | − | − | − | − | − |
| Passage 6 after treatment | − | − | − | − | − | − | − | − | − | − |
| Passage 10 after treatment | − | − | − | − | − | − | − | − | − | − |
| Passage 12 after treatment | − | − | − | − | − | − | − | − | − | − |
| Passage 15 after treatment | − | − | − | − | − | − | − | − | − | − |
| Passage 33 after treatment | − | − | − | − | − | − | − | − | − | − |

* −: contamination removed, +: contamination

From the results shown in Table 4, it can be seen that when the compound of Formula 3 was is as a reagent for removing *mycoplasma* and a filter having a pore size of 10 to 100 µm is used, the *mycoplasma* contamination can be completely removed.

The invention claimed is:
1. A method for removing *mycoplasma* contamination from cells contaminated with *mycoplasma*, the method comprising
(i) treating cells contaminated with *mycoplasma* with an enzyme solution for single cell-isolation to obtain a cell suspension;
(ii) removing cell clumps from the cell suspension obtained from the step (i); and
(iii) culturing the cell suspension obtained from the step (ii) or cells harvested from the cell suspension in a medium containing an agent having a *mycoplasma* inhibitory activity wherein the agent having a *mycoplasma* inhibitory activity comprises

(a) an extract of biomass obtained by culturing *Amphidinium klebsii* or *Amphidinium carterae*, wherein the extract is obtained by performing an extraction process which comprises: (a) extracting the biomass with a $C_1$ to $C_4$ alcohol and acetone; (b) extracting the extract obtained from the step (a) with water and ethyl acetate, followed by separating an aqueous layer; and (c) extracting the aqueous layer obtained from the step (b) with n-butanol, followed by separating an n-butanol layer; or (b) an amphidinol derivative selected from the group consisting of the compounds represented by Formula 1 to 8 below:

<Formula 1>
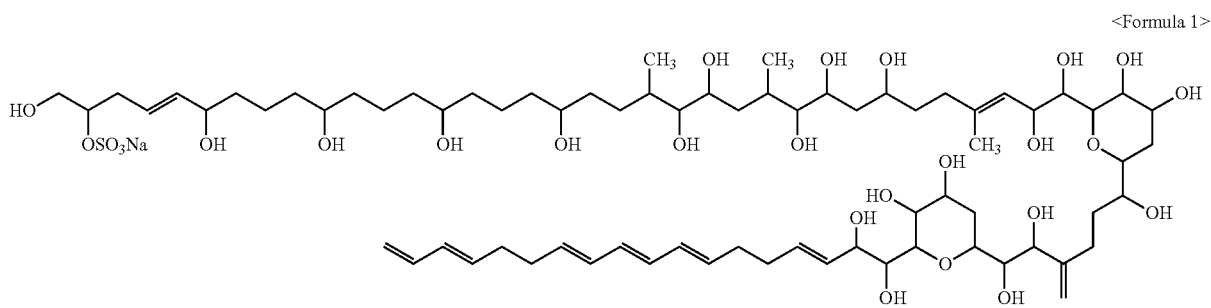

<Formula 2>
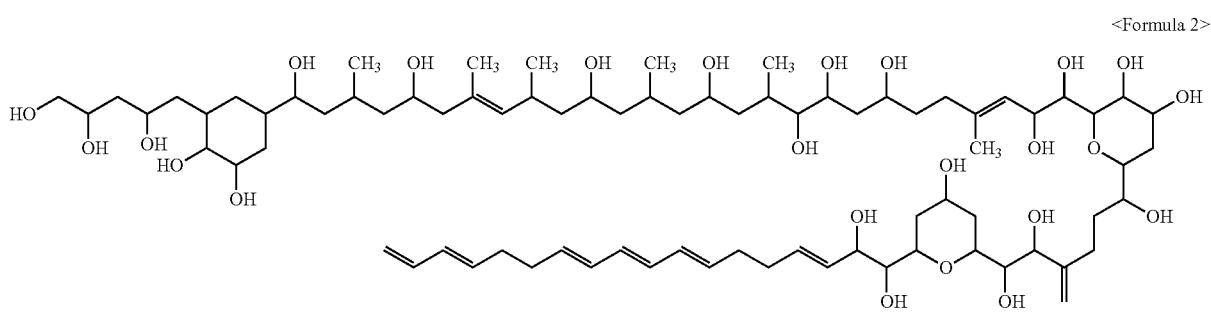

<Formula 3>
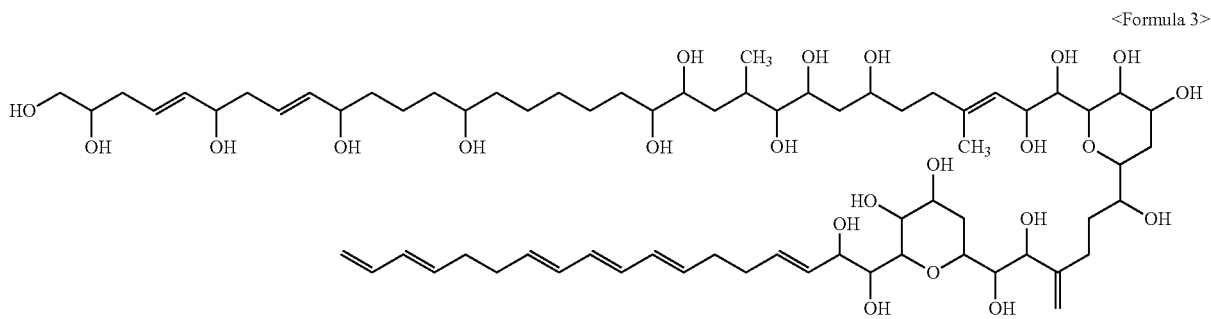

<Formula 4>
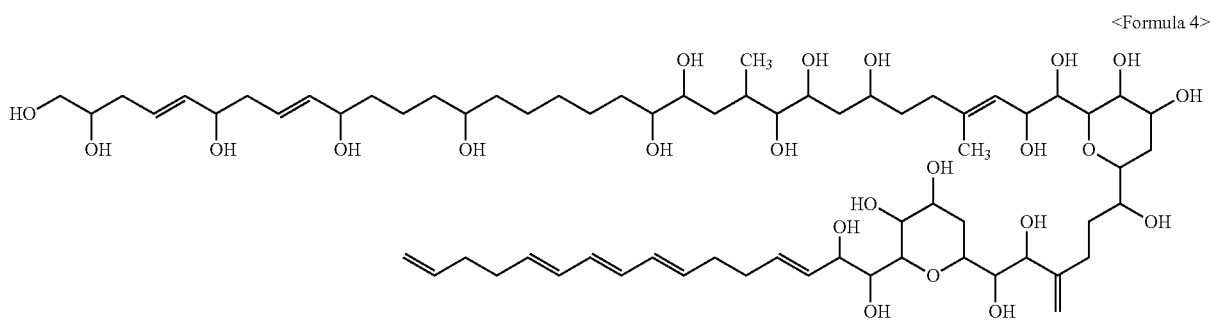

-continued

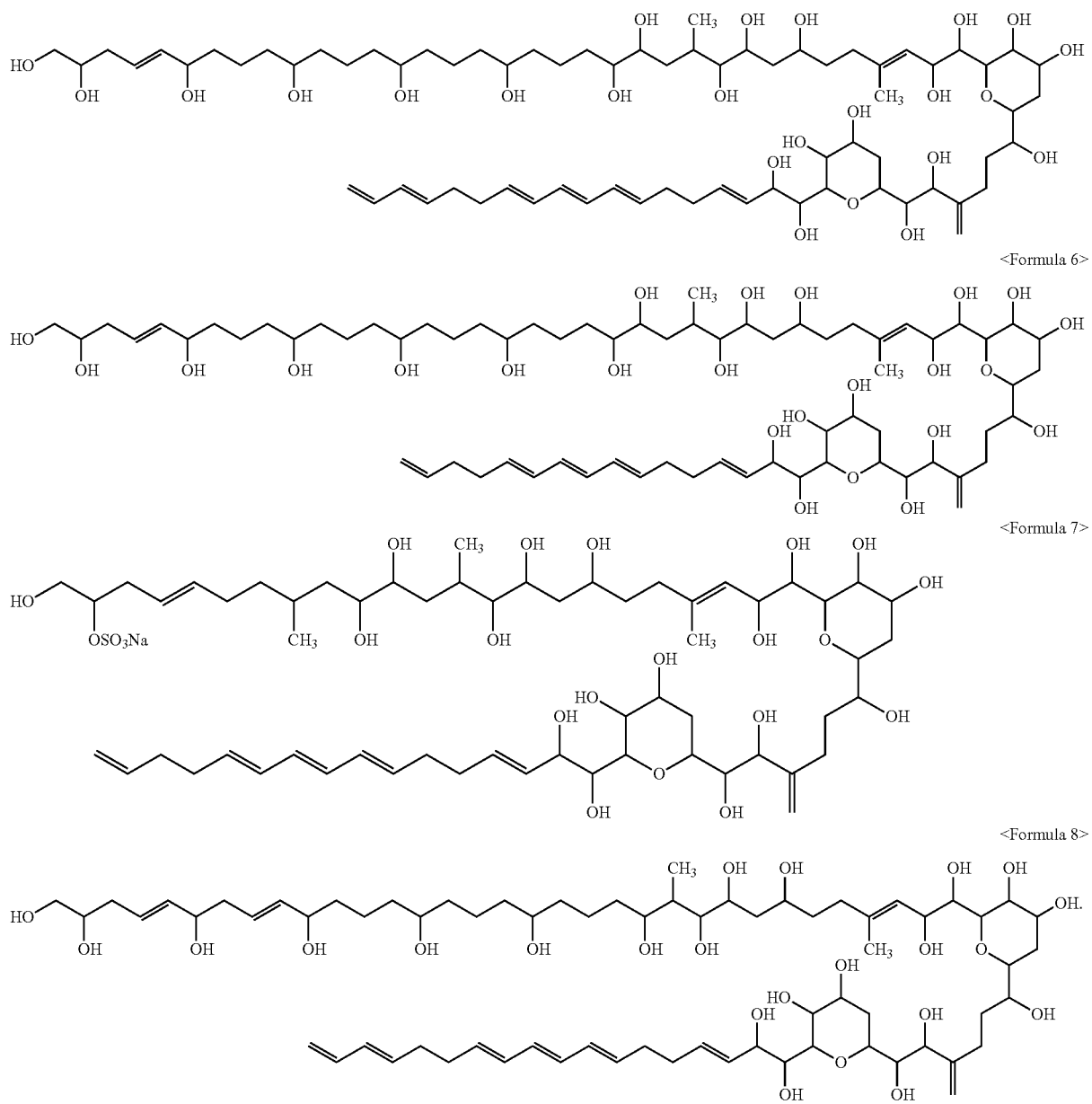

<Formula 5>

<Formula 6>

<Formula 7>

<Formula 8> thereby the cell culturing method removes *mycoplasma* contamination from cells contaminated with *mycoplasma*.

2. The method of claim 1, wherein the enzyme solution for single cell-isolation is a solution comprising trypsin and ethylenediaminetetraacetic acid.

3. The method of claim 1, wherein the step (ii) is performed by filtering the cell suspension obtained from the step (i) through a filter having a pore size of 10 to 100 μm to remove cell clumps.

4. The method of claim 1, wherein the step (i) to the step (iii) are repeatedly performed twice to four times.

5. The method of claim 1, wherein the agent having a *mycoplasma* inhibitory activity further comprises at least one selected from the group consisting of 6-methylpurine deoxyriboside, 6-methylpurin riboside, ciprofloxacin, doxycycline, rifampicin, chloramphenicol, plasmocin, clindamycin, azithromycin, clarithromycine, tetracycline, tiamulin, surfactin, alamethicin, cecropin P1, globomycin, gramicidine S, magainin 2, melittin, polymyxin B, tylosin, and valinomycin.

6. The method of claim 1, wherein the amphidinol derivative is the compound of Formula 3.

* * * * *